United States Patent [19]

McIntyre

[11] 4,340,281
[45] Jul. 20, 1982

[54] METHOD AND APPARATUS FOR ESTIMATING THE ENDOTHELIAL CELL DENSITY

[76] Inventor: David J. McIntyre, 1920 116th Ave. NE., Bellevue, Wash. 98004

[21] Appl. No.: 138,366

[22] Filed: Apr. 8, 1980

[51] Int. Cl.³ .............................................. A61B 3/10
[52] U.S. Cl. ...................................... 351/6; 351/14; 356/42
[58] Field of Search .......................... 351/6, 13, 14, 7; 356/42, 243, 39

[56] References Cited

U.S. PATENT DOCUMENTS 4,219,257 8/1980 Slappey et al. ................... 351/6 X Primary Examiner—John K. Corbin
Assistant Examiner—Rodney B. Bovernick
Attorney, Agent, or Firm—Christensen, O'Connor, Johnson & Kindness

[57] ABSTRACT

Endothelial cell density is determined by comparing the specular image of the endothelium at a predetermined magnification with a set of grids each having a plurality of apertures formed in a hexagonal, honeycomb pattern. The apertures in each of the grids are closely spaced and of predetermined size corresponding to a predetermined cell density at the predetermined magnification.

11 Claims, 2 Drawing Figures

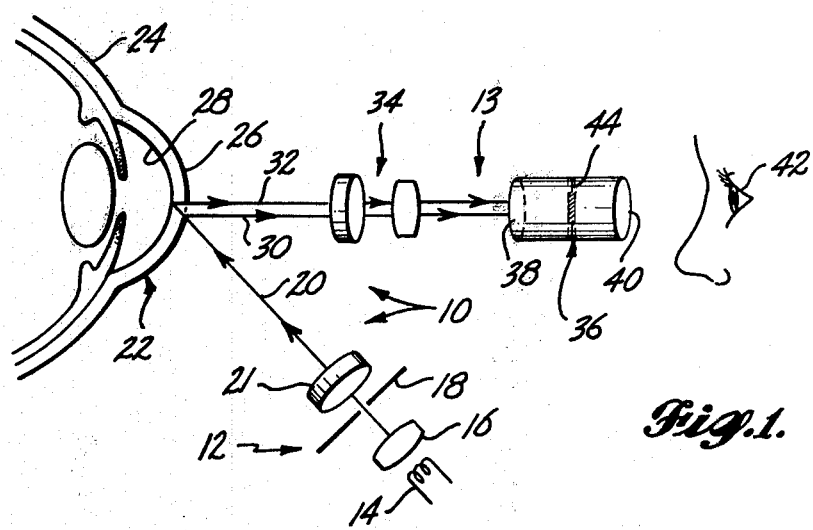
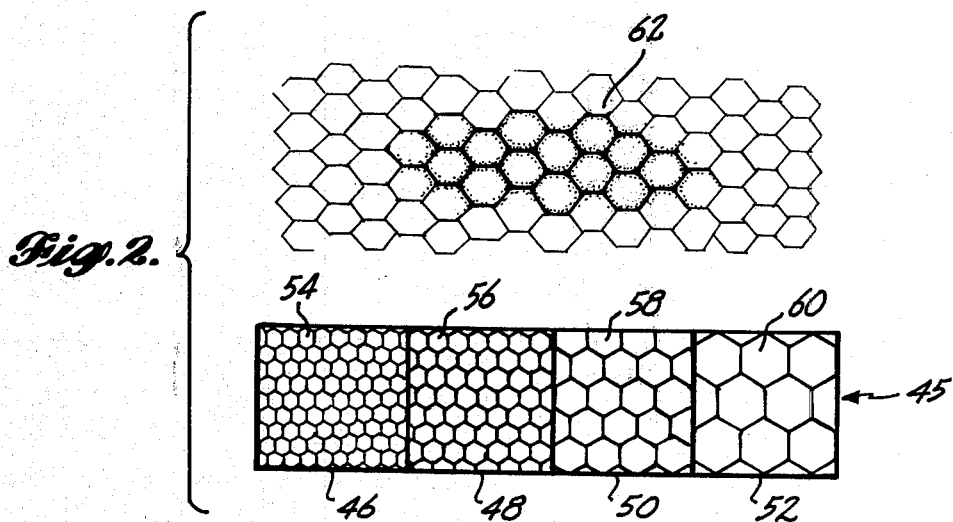

METHOD AND APPARATUS FOR ESTIMATING THE ENDOTHELIAL CELL DENSITY

BACKGROUND OF THE INVENTION

The present invention relates to method and apparatus for estimating the endothelial cell density utilizing biomicroscopic techniques.

Preoperative endothelial evaluation is a strong prognostic factor in discussing and determining the risk of complication associated with eye surgery. For example, if the cell density in the endothelium is normal, the risk of permanent damage to the endothelium during surgery is less than when the cell density has been previously reduced by injury, illness or the aging process.

Endothelial specular photomicrography has proven to be an important investigative technique. Via this technique, excellent photographs of the endothelium are available; however, while the experienced, competent technician is able to obtain satisfactory cell counts on most patients, some patients refuse or fail to cooperate. In addition, certain clear corneas are sufficiently irregular to prevent the recording of an adequate countable sample of the cell population. Additionally, the photomicrography equipment and recording technique are quite costly. Accordingly, there is a need for a less costly and less complex means of arriving at a clinically useful endothelial cell count.

It is, therefore, a broad object of the present invention to provide method and apparatus for estimating endothelial cell density. More particularly, objects of the present invention are to provide a relatively simple, relatively easy to use, and relatively inexpensive method and apparatus for estimating the endothelial cell density.

SUMMARY OF THE INVENTION

The foregoing objects, and other objects that will become apparent to one of ordinary skill after reading the following specification, are provided in a method for estimating the endothelial cell count or density and an apparatus for achieving the same. The method comprises a first step of positioning the specular image of the endothelium at a predetermined magnification adjacent the image of a set of grids each having a plurality of apertures therein. Each grid in the set has a plurality of closely spaced apertures of predetermined size corresponding to a predetermined cell density at the predetermined magnification. The second step of the method comprises comparing the cell pattern of the specular image with each grid in the set to determine which grid most closely corresponds to the cell pattern.

The method is easily achieved by inserting a reticle in a slit lamp biomicroscope, the latter of which is a common instrument ordinarily used by ophthalmologists in eye examinations. The slit lamp biomicroscope has an ocular including both an eye lens and a field lens. The improvement comprises a reticle plate that is positioned between the eye and field lenses at a distance from the eye lens equal to the focal length of the eye lens. The reticle includes a plurality of grids each having a plurality of closely spaced apertures of equal and predetermined size corresponding to a predetermined endothelial cell density at a predetermined magnification of the specular image of the endothelium. Preferably, the grids have a hexagonal, honeycomb pattern. Preferably four grids are utilized corresponding to cell densities of 500, 1000, 2000, and 4000 cells per square millimeter.

BRIEF DESCRIPTION OF THE DRAWINGS

A better understanding of the present invention can be derived by reading the ensuing specification in conjunction with the accompanying drawings wherein:

FIG. 1 is a line drawing of a slit lamp biomicroscope employing the reticle of the present invention; and FIG. 2 is an enlarged view of the superimposed image of the reticle and the adjacent specular image of the endothelium.

DETAILED DESCRIPTION OF THE INVENTION

Referring first to FIG. 1, the slit lamp biomicroscope generally designated 10 simply comprises two components, a light source 12 and a microscope 13. The slit lamp biomicroscope is very simply illustrated in a line drawing in FIG. 1. One of ordinary skill will realize that the optics actually employed in such biomicroscopes are somewhat more complicated than those simply shown in the figure. The light source consists, in essence, of a point source 14 of light, schematically illustrated by a filament. The light from the source 14 is directed through a condensing lens 16. From the condensing lens 16 the light is directed through an adjustable stop 18 that transforms the light beam into a narrow band of light or slit beam designated by the line 20. The slit beam 20 is directed through focusing optics 21, and thence toward the cornea 22 of an eye 24. The slit beam 20 is focused upon the cornea 22. Specular reflections are obtained both from the epithelium 26 and from the endothelium 28. These reflections form respective specular images as indicated by lines 30 and 32. The specular images are then directed into the objective and magnification changer 34 of the slit lamp biomicroscope. The objective, of course, magnifies the specular images and directs them toward the ocular 36 of the biomicroscope. The ocular 36 comprises a field lens 38 and an eye lens 40 through which the observer 42 can observe the magnified specular images of the epithelium 26 and the endothelium 28.

A reticle plate 44 carrying the reticle of the present invention is interposed between the eye lens 40 and the field lens 38 of the ocular 36. In the Zeiss slit lamp biomicroscope, for example, the reticle plate is spaced from the eye lens 40 by a distance equivalent to the focal length of the eye lens 40. Thus, the observer 42 can adjust the slit lamp so that he can simultaneously view the specular image of the endothelium 28, for example, and the reticle on the reticle plate 44 in side-by-side relationship.

Referring to FIG. 2, the reticle 45 preferably comprises a set of four rectangular grids 46, 48, 50, and 52. Each of the grids 46 through 52 carries a grid pattern comprising a plurality of apertures 54, 56, 58, and 60, respectively. Most preferably, the apertures are hexagonal in shape and are arranged in a honeycomb pattern. The hexagonal apertures within each grid are equally sized. From grid to grid the apertures are graduated in size to correspond to various endothelial cell densities observed in the specular image at a predetermined magnification. For example, the four grids can carry grid patterns corresponding to endothelial cell densities of 500, 1000, 2000, and 4000 cells per square millimeter at a predetermined magnification value of the biomicroscope. It is preferred, for example, to view the endothelium at a magnification of 40×. This magnification is chosen as it is standard magnification on slit lamp biomicroscopes and because the magnification is great enough so that the individual cells of the endothelium can be readily observed.

In use, the reticle of the present invention is inserted into the ocular as described above. Estimation of the endothelial cell density is best performed prior to installation of any medication and prior to any corneal manipulations, such as contact tonometry. If a broken mucoid tear film is present, the image may be greatly enhanced by instillation of a suitable artificial tear. The patient is then seated at the slit lamp biomicroscope with the forehead firmly applied to the headrest normally associated with the slit lamp biomicroscope. The patient is requested to hold his gaze in a desired, predetermined direction, but reminded to continue normal blinking to assure a continued tear layer. The slit lamp is then brought into position at a magnification of 10× with the slit beam at approximately a 45° angle to obtain the epithelial specular reflection. The intense epithelial specular reflection is then centered in the microscope and the magnification changed to 40×. The slit beam is then adjusted to approximately equal the width of reticle pattern. Additionally, the angle of the lamp at that time is adjusted to maximize the endothelial specular image 62 (FIG. 2) and to position the specular image adjacent the image of the reticle 45 so that the two images can be compared on a side-by-side basis. The endothelial cell pattern is then examined for uniformity of size, regularity of shape, definition of boundaries, and compared with the reticle pattern to estimate cell density. In this manner, clinically useful estimates of endothelial cell density are readily obtained. Additionally, in a very short time and a very low cost, a large number of endothelial cells can be examined across various corneal diameters.

The present invention has been disclosed in relation to preferred method and apparatus for carrying out the invention. One of ordinary skill after reading the foregoing specification will be able to effect various alterations, substitutions of equivalents, and other changes without departing from the broad concepts imparted herein. Accordingly, it is intended that the Letters Patent granted hereon be limited only by the definition contained in the appended claims and equivalents thereof.

The embodiments of the invention in which an exclusive property or privilege is claimed are defined as follows:

1. A method for estimating the endothelial cell count comprising:
   positioning the specular image of the endothelium at a predetermined magnification adjacent the image of a set of grids having a plurality of apertures therein, each grid in said set having a plurality of closely spaced apertures of predetermined size corresponding to a predetermined cell density at said predetermined magnification, and
   comparing the cell pattern of said image with each grid in said set to determine which grid most closely corresponds to the cell spacing in said cell pattern.

2. The method of claim 1 wherein said apertures are in a hexagonal, honeycomb pattern.

3. The method of claim 2 wherein said predetermined magnification is 40×.

4. The method of claim 3 wherein said set comprises four grids corresponding to cell densities of 500, 1000, 2000, and 4000 cells per square millimeter.

5. In a slit lamp biomicroscope having an ocular including an eye lens and a field lens, an improved reticle comprising:
   a reticle plate positioned between said eye and field lenses and being spaced from said eye lens by a distance substantially the same as the focal length of said eye lens, said reticle including a plurality of grids having a plurality of closely spaced apertures of equal and predetermined size corresponding to a predetermined endothelial cell density at a predetermined magnification of the specular image of the endothelium.

6. The reticle of claim 5 wherein said grids are in a hexagonal, honeycomb pattern.

7. The reticle of claim 6 wherein said reticle includes grids corresponding to cell densities of 500, 1000, 2000, and 4000 cells per square millimeter.

8. The reticle of claim 7 wherein said predetermined magnification is 40×.

9. A reticle for use in slit lamp biomicroscopy comprising a transparent plate bearing a reticle, said reticle including a plurality of grids each of said grids having a plurality of closely spaced apertures of equal and predetermined size corresponding to a predetermined endothelial cell density at a predetermined magnification of the specular image of the endothelium.

10. The reticle of claim 9 wherein said grids are in a hexagonal, honeycomb pattern.

11. The reticle of claim 10 wherein said grids correspond at least to cell densities 500, 1000, 2000, and 4000 cells per square millimeter.

* * * * *